US008367073B2

(12) United States Patent
Mendelsohn et al.

(10) Patent No.: US 8,367,073 B2
(45) Date of Patent: *Feb. 5, 2013

(54) CHLORAMPHENICOL ACETYL TRANSFERASE (CAT)-DEFECTIVE SOMATOSTATIN FUSION PROTEIN AND USES THEREOF

(75) Inventors: Andrew R. Mendelsohn, Sunnyvale, CA (US); Keith N. Haffer, Garretson, SD (US); James Larrick, Sunnyvale, CA (US)

(73) Assignee: Braasch Biotech, LLC, Garretson, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/069,592

(22) Filed: Mar. 23, 2011

(65) Prior Publication Data

US 2012/0076806 A1 Mar. 29, 2012

Related U.S. Application Data

(60) Continuation of application No. 12/703,631, filed on Feb. 10, 2010, now Pat. No. 7,943,143, which is a division of application No. 12/198,579, filed on Aug. 26, 2008, now Pat. No. 7,722,881, which is a continuation of application No. PCT/US2008/068195, filed on Jun. 25, 2008.

(51) Int. Cl.
*A61K 39/00* (2006.01)
(52) U.S. Cl. ................... 424/198.1; 424/185.1; 530/311
(58) Field of Classification Search ........................ None
See application file for complete search history.

(56) References Cited

U.S. PATENT DOCUMENTS

| 4,446,235 | A | 5/1984 | Seeburg |
| 4,601,980 | A | 7/1986 | Goeddel et al. |
| 6,025,368 | A | 2/2000 | Mascarenhas et al. |
| 6,316,004 | B1 | 11/2001 | Lunin et al. |
| 7,722,881 | B2 | 5/2010 | Mendelsohn et al. |
| 7,943,143 | B2 | 5/2011 | Mendelsohn et al. |
| 2007/0048860 | A1 | 3/2007 | Schlom et al. |
| 2007/0249532 | A9 | 10/2007 | Guyon et al. |
| 2008/0081068 | A1 | 4/2008 | Oberegger et al. |
| 2009/0324629 | A1 | 12/2009 | Mendelsohn et al. |
| 2010/0136037 | A1 | 6/2010 | Mendelsohn et al. |

FOREIGN PATENT DOCUMENTS

| EP | 0645454 | 1/1997 |
| KR | 1990-7000505 | 8/1990 |
| WO | WO 89/04326 | 5/1989 |
| WO | WO 2005/066344 | 7/2005 |
| WO | WO 2009/157926 | 12/2009 |
| WO | WO 2009/158395 | 12/2009 |

OTHER PUBLICATIONS

Araki et al. (2008) "Effects of Pravastatin on Obesity, Diabetes, and Adiponectin in Diet-induced Obese Mice" Obesity 16:2068-2073.
Chothia and Lesk (1986) "The Relation Between the Divergence of Sequence and Structure in Proteins" The EMBO Journal, 5(4):823-826.
Danoff et al. (1993) "Intracellular degradation of prohormone-chloramphenicol-acetyl-transferase chimeras in a pre-lysosomal compartment" Eur. J. Biochem 218(3):1063-1070.
Drackley, J.K. (2004) "Physiological Adaptations in Transition Dairy Cows" Proc. Minnesota Dairy Herd Health Conf., St. Paul, MN. University of Minnesota, St. Paul. pp. 74-87.
Drozdowski et al. (2006) "Intestinal Mucosal Adaptation" World of Gastroenterol., 12(29):4614-4627.
Fortier et al. (2002) "Insulin-Like Growth Factor-I Enhances Cell-Based Repair of Articular Cartilage" Journal of Bone and Joint Surgery, 84-B(2):276-288.
Greenspan and Di Cera (1999) "Defining Epitopes: It's Not As Easy As It Seems" Nature Biotechnology, 17:936-937.
Jaffe et al. (1996) "Endogenous Growth Hormone (GH)-Releasing Hormone is Required for GH Responses to Pharmacological Stimuli" J. Clin. Investigation, 97(4):934-940.
Lewendon and Shaw (1993) "The $pK_a$ of the catalytic histidine residue of chloramphenicol acetyltransferase" Biochem. J. 290:15-19.
Lewendon A. et al., (1994) "Replacement of Catalytic Histidine-195 of Chloramphenicol Acetyl Transferase: Evidence for a General Role for Glutamate" Biochemistry 33(7):1944-50.
Liang et al. (2008) "Construction and evaluation of the eukaryotic expression plasmid encoding two copies of somatostatin genes fused with hepatitis B surface antigen gene S" Vaccine 26(23):2935-2941.
Lin X.W. et al., (1998) "Evolution of Neuroendocrine Peptide Systems: Gonadotropin-releasing Hormone and Somatostain" Comp. Biochem Physiol. C. 119(3):375-88.
Liu and LeRoith (1999) "Insulin-Like Growth Factor I is Essential for Postnatal Growth in Response to Growth Hormone" Endocrinology, 140(11):5178-5184.
Mikayama et al. (1993) "Molecular Cloning and Functional Expression of a cDNA Encoding Glycosylation-Inhibiting Factor" Proc. Natl. Acad. Sci. USA, 90:10056-10060.
Muderhwa et al. (1999) "Oil-in-water liposomal emulsions: Characterization and potential use in vaccine delivery" Journal of Pharmaceutical Sciences 88(12):1332-1339.
Notice of Allowance Jan. 28, 2010 with respect to U.S. Appl. No. 12/198,579.
Office Action Nov. 16, 2009 with respect to U.S. Appl. No. 12/198,579.
Patel and Srikant (1999) "Somatostatin and It's Receptors" Adv Mol Cell Endocrinol., 3:43-73.
Reichlin S., ed. (1987) Somatostatin: Basic and Clinical Status, Plenum Press, New York and London (pp. 3-50, 121-136, 146-156, 169-182, 221-228, 267-274).
Rudinger (1976) "Characteristics of the Amino Acids as Components of a Peptide Hormone Sequence" Peptide Hormones. Biol. Council., pp. 5-7.

(Continued)

*Primary Examiner* — Jennifer Graser
(74) *Attorney, Agent, or Firm* — Merchant & Gould, P.C.

(57) ABSTRACT

Chimeric somatostatin-based polypeptides, polynucleotides used to encode the polypeptides, the methods for isolating and producing the polypeptides and the uses thereof are provided. In addition, low cost adjuvants for enhanced immunogenic response are provided. Vaccinations that include both chimeric somatostatin-based polypeptides and novel adjuvants are included, useful in facilitating farm animal productivity.

17 Claims, 4 Drawing Sheets

OTHER PUBLICATIONS

Samson et al. (2008) "Gene Therapy for Diabetes: Metabolic Effects of Helper-dependent Adenoviral Exendin 4 Expression in a Diet-induced Obesity Mouse Model" Mol. Ther. 16(11):1805-1812.

Spencer G.S. (1985) "Hormonal Systems Regulating Growth. A Review" Livestock Production Science, 12:31-46.

Tropea et al., (2009) "Partial Reversal of Rett Syndrome-Like Symptoms in MeCP2 Mutant Mice" PNAS 106(6):2029-2034.

Vickers et al. (2002) "Adult Growth Hormone Treatment Reduces Hypertension and Obesity Induced by an Adverse Prenatal Environment" Journal of Endocrinology, 175:615-623.

White et al., (2000) "Characterization of Chloramphenicol and Florfenicol Resistance in *Escherichia coli* Associated with Bovine Diarrhea" J. of Clinical Microbiology 38(12):4593-4598.

CHIMERIC POLYPEPTIDE TREATED

| Cow# | MY D10 | MY D15 | Increase Yield | % Increase |
|---|---|---|---|---|
| 3361 | 30 | 34 | +4 Lbs | 13% |
| 4222 | 32 | 40 | +8 Lbs | 25% |
| 5961 | 40 | 55 | +15 Lbs | 38% |
| 6141 | 20 | 29 | +9 Lbs | 45% |
| 6142 | 30 | 35 | +5 Lbs | 17% |
| 6540 | 24 | 25 | +1 Lbs | 4% |
| Mean | 29.33 | 36.33 | +7.0 Lbs | 23.7% |

FIG. 3A

BST

| Cow # | Pre-Treatment (lbs) | Post-Treatment Period (Mean lbs) | % Change |
|---|---|---|---|
| 983 | 56.3 | 55.7 | -1% |
| 3361 | 27.7 | 33.2 | 20% |
| 4222 | 34.5 | 36.8 | 7% |
| 5961 | 42.3 | 44.8 | 6% |
| 6141 | 29.8 | 25.3 | -15% |
| 6142 | 34.5 | 27 | -22% |
| 6490 | 30.5 | 33.3 | 9% |
| 6540 | 11 | 23.8 | 8% |
| 6556 | 13.8 | 14.5 | 5% |
| Mean | 32.4 | 32.7 | 2% |

FIG. 3B

CHLORAMPHENICOL ACETYL TRANSFERASE (CAT)-DEFECTIVE SOMATOSTATIN FUSION PROTEIN AND USES THEREOF

RELATED APPLICATIONS

This application is a continuation of U.S. patent application Ser. No. 12/703,631, filed Feb. 10, 2010, now U.S. Pat. No. 7,943,143, entitled "Chloramphenicol Acetyl Transferase (CAT)-Defective Somatostatin Fusion Protein And Uses Thereof", which is a divisional of U.S. patent application Ser. No. 12/198,579, filed Aug. 26, 2008, now U.S. Pat. No. 7,722,881, entitled "Chloramphenicol Acetyl Transferase (CAT)-Defective Somatostatin Fusion Protein And Uses Thereof" which is a continuation of PCT/US2008/068195, filed on Jun. 25, 2008, entitled "Chloramphenicol Acetyl Transferase (CAT)-Defective Somatostatin Fusion Protein And Uses Thereof" each of which is incorporated herein by reference in its entirety.

TECHNICAL FIELD

The present invention relates to chimeric somatostatin-based polypeptides, polynucleotides used to encode the polypeptides, the means for isolating and producing the polypeptides, and to the uses thereof. The present invention also relates to novel adjuvants and immunization compositions for enhanced immunogenicity of, for example, chimeric somatostatin-based polypeptides of the invention as well as to other like antigens.

BACKGROUND OF THE INVENTION

Somatostatin (also known as growth hormone inhibiting hormone or GHIH) is a peptide hormone produced in the hypothalamus as well as certain portions of the digestive system. Somatostatin is generally involved in regulation of the endocrine system via interactions with G-protein-coupled somatostatin receptors. This somatostatin-based signaling cascade leads to a number of actions spread throughout the body.

Relevant to aspects of the present invention, somatostatin is known to inhibit the release of growth hormone and thyroid stimulating hormone from the anterior pituitary. (Patel Y C and Srikant C B, Somatostatin and its receptors Adv Mol Cell Endocrinol, 1999. 3 43-73). Other hormones inhibited by somatostatin include insulin, glucagon, secretin, gastrin, pepsin, maletin, etc. (Patel Y C and Srikant C B Somatostatin and its receptors Adv Mol Cell Endocrinol, 1999. 3 43-73). The ability of somatostatin to regulate so many factors/hormones necessary for growth and utilization of food has made somatostatin a central target for controlling animal growth in the animal husbandry field, i.e., inhibiting somatostatin results in increased levels of growth hormone being present in a target animal and thereby results in animals with enhanced capacity to produce milk, to provide greater amounts of meat, etc.

In particular, immunization of animals to somatostatin has been recognized as a means of neutralizing somatostatin in a target animal and thereby removing somatostatin's normal inhibitory effects on various aspects of the animal's productivity, e.g., milk production in a dairy cow. Reichlin S., ed., 1987, Somatostatin, Basic and Clinical Status, Plenum Press, New York (pp 3-50, 121-136, 146-156, 169-182, 221-228, 267-274) Spencer G. S., 1985, Hormonal systems regulating growth, review, Livestock Production Science, 12, 31-46. Importantly, these somatostatin-based immunization procedures avoid the direct use of anabolic hormones, e.g., growth hormone, and the like, in the animal and allow for small changes in the concentration of the endogenous anabolic factors and thereby provide ecologically pure food products.

Somatostatin is known to have a relatively short half-life in the blood. In order to enhance the immunologic effects of somatostatin, immunization protocols have been developed to enhance the protein's half-life by conjugating somatostatin to target carrier proteins. These conjugated somatostatin proteins are designed to have increased half-life and increased antigenicity in the blood and therefore provide enhanced benefits (especially in light of the cost of preparing somatostatin). For example, chimeric somatostatin proteins are disclosed in U.S. Pat. No. 6,316,004, (and corresponding European Patent EP0645454) where various conjugated somatostatin-containing proteins are shown to have increased antigenicity and function with regard to productivity of farm animals as compared to other conventional immunization or anabolic hormone-based procedures.

However, lower dose, higher antigenicity based immunization compositions and procedures are needed to improve overall productivity and timeliness in the animal husbandry field. The present invention is directed toward providing these more antigenic and functionally active somatostatin-based immunization compounds, compositions and procedures.

Against this backdrop the following disclosure is provided.

SUMMARY OF THE INVENTION

The present invention provides novel polypeptides, and the polynucleotides that encode them, having enhanced immunogenicity of somatostatin. Polypeptides of the invention include somatostatin-14 fused to a substantially inactivated chloramphenicol acetyl transferase protein via a functionally optimized linker. The chimeric polypeptides of the invention provide highly effective and low cost materials for use in the animal husbandry field, as is described in more detail below. Embodiments of the invention include the amino acid and nucleic acid sequences as defined in SEQ ID NOs: 1-15.

The present invention also provides production and purification procedures for making the chimeric polypeptides of the invention in an endotoxin free and highly functional state. Endotoxin free polypeptides provide a substantial and unexpected advantage for use in certain target animals, where small amounts of endotoxin, typically thought advantageous for eliciting an immunogenic response, actually lead to significant functional disadvantage. This is particularly the case when polypeptides of the invention are used to immunize United States bred and raised dairy cows. In addition, because the chimeric polypeptides of the invention show enhanced function as compared to conventional materials, smaller and lower number of doses are used to immunize target animals. This decrease in required amounts also provides a resultant reduction of endotoxin in vaccines of the invention. The combination of endotoxin free isolation and smaller use amount of the chimeric polypeptides of the invention allows for substantially endotoxin free vaccines to be used herein.

The invention also provides adjuvant compositions having enhanced function and safety as compared to conventional adjuvant materials. Adjuvants herein do not contain animal-derived materials and are free of most known chemical carcinogens, e.g., benzene and other like materials. Adjuvant compositions herein have proven to be unexpectedly effective at eliciting immune response when combined with target antigens.

The invention further provides vaccines containing the chimeric polypeptides of the invention with adjuvant compositions of the invention. Vaccines herein are used for inducing immune responses in vaccinated mammals and avian, for example, target farm animals. Illustrative farm animals for use herein include: dairy cows, pigs, sheep, goats, turkeys, rabbits, and bull calves. In some aspects the polypeptides of the invention are prepared and purified with low or no associated endotoxin. These vaccines have been optimized to elicit safe and enhanced immunogenic reactions in the target animal.

The invention further includes methods for vaccinating target mammals and avians using the vaccines of the invention. Illustrative methods are provided for vaccination of dairy cows to enhance milk production in a safe (for both animal and end-user), cost-effective and highly useful manner. Other illustrative methods include vaccination of piglets, sheep, turkeys, goats, rabbits or bull calves to enhance meat (and particularly lean meat) production in a target animal in a safe and cost-effective manner.

These and various other features and advantages of the invention will be apparent from a reading of the following detailed description and a review of the appended claims

BRIEF DESCRIPTION OF THE DRAWINGS

FIGS. 3A and 3B are tables showing milk production in liters per day of vaccinated (using vaccines as described in the Examples) and control dairy cattle (BSY). Each cow had a specific number identification as shown in each table.

Figure 1:
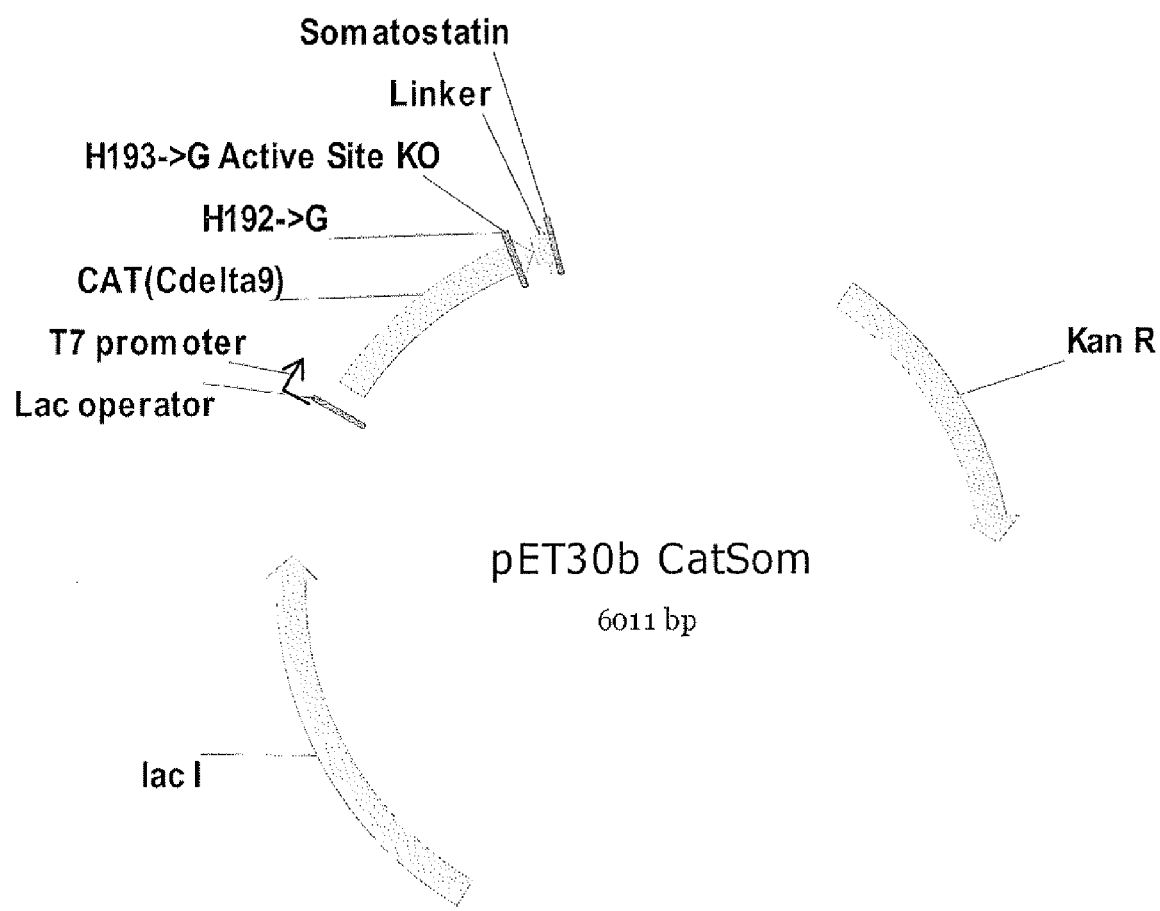
FIG. 1 is an illustrative schematic of a pET30b CatSom plasmid in accordance with embodiments of the present invention. The plasmid includes a Kanamycin resistance marker, a Lac operator, T7 promoter, CAT coding sequence all in accordance with embodiments of the invention, a linker region in accordance with the invention herein and a somatostatin encoding region in accordance with the invention are also included.

IDENTIFICATION OF SEQUENCES AND
SEQUENCE IDENTIFIERS

SEQ ID NO: 1
AGCKNFFWKTFTSC

SEQ ID NO: 2
GCTGGCTGCAAGAATTTCTTCTGGAAGACTTTCACATCCTGT

SEQ ID NO: 3 (His192->Gly, His193->Gly):
Atggagaaaaaaatcactggatataccaccgttgatatatcccaatggcatcgtaaagaacattttgaggcatttcagtcagttgctcaatgta cctataaccagaccgttcagctggatattacggccttttaaagaccgtaaagaaaaataagcacaagttttatccggcctttattcacattcttg cccgcctgatgaatgctcatccggaattccgtatggcaatgaaagacggtgagctggtgatatgggatagtgttcacccttgttacaccgtttt ccatgagcaaactgaaacgttttcatcgctctggagtgaataccacgacgatttccggcagtttctacacatatattcgcaagatgtggcgtgtt acggtgaaaacctggcctatttccctaaagggtttattgagaatatgttttttcgtctcagccaatccctgggtgagtttcaccagttttgatttaaac gtggccaatatggacaacttcttcgccccgttttcaccatgggcaaatattatacgcaaggcgacaaggtgctgatgccgctggcgattcag gttggtggtgccgtttgtgatggcttccatgtcggccgtatgcttaatgaactgcagcag SEQ ID NO: 4: (His192->Gly, His193->Gly):
Mekkitgyttvdisqwhrkehfeafqsvaqctynqtvqlditaflktvkknkhkfypafihilarlmnahpefrmamkdgelviwds vhpcytvfheqtetfsslwseyhddfrqflhiysqdvacygenlayfpkgfienmffvsanpwvsftsfdlnvanmdnffapvftmg kyytqgdkvlmplaiqvggavcdgfhvgrmlnelqq SEQ ID NO: 5 (His193->Gly)
Atggagaaaaaaatcactggatataccaccgttgatatatcccaatggcatcgtaaagaacattttgaggcatttcagtcagttgctcaatgta cctataaccagaccgttcagctggatattacggccttttaaagaccgtaaagaaaaataagcacaagttttatccggcctttattcacattcttg cccgcctgatgaatgctcatccggaattccgtatggcaatgaaagacggtgagctggtgatatgggatagtgttcacccttgttacaccgtttt ccatgagcaaactgaaacgttttcatcgctctggagtgaataccacgacgatttccggcagtttctacacatatattcgcaagatgtggcgtgtt acggtgaaaacctggcctatttccctaaagggtttattgagaatatgttttttcgtctcagccaatccctgggtgagtttcaccagttttgatttaaac gtggccaatatggacaacttcttcgccccgttttcaccatgggcaaatattatacgcaaggcgacaaggtgctgatgccgctggcgattcag gttcatggtgccgtttgtgatggcttccatgtcggccgtatgcttaatgaactgcagcag SEQ ID NO: 6 (1 His193->Ala)
Atggagaaaaaaatcactggatataccaccgttgatatatcccaatggcatcgtaaagaacattttgaggcatttcagtcagttgctcaatgta cctataaccagaccgttcagctggatattacggccttttaaagaccgtaaagaaaaataagcacaagttttatccggcctttattcacattcttg cccgcctgatgaatgctcatccggaattccgtatggcaatgaaagacggtgagctggtgatatgggatagtgttcacccttgttacaccgtttt ccatgagcaaactgaaacgttttcatcgctctggagtgaataccacgacgatttccggcagtttctacacatatattcgcaagatgtggcgtgtt -continued acggtgaaaacctggcctatttccctaaagggtttattgagaatatgttttcgtctcagccaatccctgggtgagtttcaccagttttgatttaaac gtggccaatatggacaacttcttcgccccgttttcaccatgggcaaatattatacgcaaggcgacaaggtgctgatgccgctggcgattcag gttcatgctgccgtttgtgatggcttccatgtcggccgtatgcttaatgaactgcagcag SEQ ID NO: 7 (1 His+CAT wt)
Atggagaaaaaaatcactggatataccaccgttgatatatcccaatggcatcgtaaagaacattttgaggcatttcagtcagttgctcaatgta cctataaccagaccgttcagctggatattacggcctttttaaagaccgtaaagaaaaataagcacaagttttatccggcctttattcacattcttg cccgcctgatgaatgctcatccggaattccgtatggcaatgaaagacggtgagctggtgatatgggatagtgttcacccttgttacaccgtttt ccatgagcaaactgaaacgttttcatcgctctggagtgaataccacgacgatttccggcagtttctacacatatattcgcaagatgtggcgtgtt acggtgaaaacctggcctatttccctaaagggtttattgagaatatgttttcgtctcagccaatccctgggtgagtttcaccagttttgatttaaac gtggccaatatggacaacttcttcgccccgttttcaccatgggcaaatattatacgcaaggcgacaaggtgctgatgccgctggcgattcag gttcatggtgccgtttgtgatggcttccatgtcggcagaatgcttaatgaactgcagcag SEQ ID NO: 8 (one H->G):
Mekkitgyttvdisqwhrkehfeafqsvaqctynqtvqlditaflktvkknkhkfypafihilarlmnahpefrmamkdgelviwds vhpcytvfheqtetfsslwseyhddfrqflhiysqdvacygenlayfpkgfienmffvsanpwvsftsfdlnvanmdnffapvftmg kyytqgdkvlmplaiqvhgavcdgfhvgrmlnelqq SEQ ID NO: 9 (H->A)
Mekkitgyttvdisqwhrkehfeafqsvaqctynqtvqlditaflktvkknkhkfypafihilarlmnahpefrmamkdgelviwds vhpcytvfheqtetfsslwseyhddfrqflhiysqdvacygenlayfpkgfienmffvsanpwvsftsfdlnvanmdnffapvftmg kyytqgdkvlmplaiqvhaavcdgfhvgrmlnelqq SEQ ID NO: 10
tgggaactgcaccgttctggtccacgcccgcgccctcgcccacgtccggaattcatg SEQ ID NO: 11
welhrsgprprprprpefm SEQ ID NO: 12
welhrsgp(rp)$_n$efm
where n > 1

SEQ ID NO: 13
Atggagaaaaaaatcactggatataccaccgttgatatatcccaatggcatcgtaaagaacattttgaggcatttcagtcagttgctcaatgta cctataaccagaccgttcagctggatattacggcctttttaaagaccgtaaagaaaaataagcacaagttttatccggcctttattcacattcttg cccgcctgatgaatgctcatccggaattccgtatggcaatgaaagacggtgagctggtgatatgggatagtgttcacccttgttacaccgtttt ccatgagcaaactgaaacgttttcatcgctctggagtgaataccacgacgatttccggcagtttctacacatatattcgcaagatgtggcgtgtt acggtgaaaacctggcctatttccctaaagggtttattgagaatatgttttcgtctcagccaatccctgggtgagtttcaccagttttgatttaaac gtggccaatatggacaacttcttcgccccgttttcaccatgggcaaatattatacgcaaggcgacaaggtgctgatgccgctggcgattcag gttggtggtgccgtttgtgatggcttccatgtcggccgtatgcttaatgaactgcagcagtgggaactgcaccgttctggtccacgcccgcgc cctcgcccacgtccggaattcatggccggctgcaagaacttcttttggaaaacctttacgagctgc SEQ ID NO: 14
mekkitgyttvdisqwhrkehfeafqsvaqctynqtvqlditaflktvkknkhkfypafihilarlmnahpefrmamkdgelviwdsv hpcytvfheqtetfsslwseyhddfrqflhiysqdvacygenlayfpkgfienmffvsanpwvsftsfdlnvanmdnffapvftmgk yytqgdkvlmplaiqvggavcdgfhvgrmlnelqqwelhrsgprprprprpefmagcknffwktftsc SEQ ID NO: 15
mekkitgyttvdisqwhrkehfeafqsvaqctynqtvqlditaflktvkknkhkfypafihilarlmnahpefrmamkdgelviwdsv hpcytvfheqtetfsslwseyhddfrqflhiysqdvacygenlayfpkgfienmffvsanpwvsftsfdlnvanmdnffapvftmgk yytqgdkvlmplaiqvhhavcdgfhvgrmlnelqqwelhrsgprprprprpefmagcknffwktftsc

DETAILED DESCRIPTION OF THE INVENTION

Embodiments of the present invention provide chimeric polypeptides, and nucleic acid constructs that encode the same, having enhanced immunogenicity of somatostatin. Embodiments herein include methods for preparing the chimeric protein as well as methods for using the chimeric protein to increase certain productivity of target farm animals, and especially for increasing milk production in dairy cows and meat production of cattle, pigs, sheep, rabbits, goats, bull calves, etc.

Embodiments of the present invention also include novel adjuvants for use with the chimeric proteins of the invention for enhanced immunogenicity in a target animal, enhanced safety for the target animal being vaccinated and enhanced safety for a user of the target animal, i.e., consumer of the vaccinated animal or consumer of a product from the vaccinated animal.

In one aspect, the invention provides chimeric somatostatin protein designed for enhanced immunogenicity of somatostatin. Chimeric somatostatin protein embodiments include an amino acid sequence of somatostatin-14 linked by a linker sequence to a substantially inactivated chloramphenicol acetyl transferase (CAT) truncated protein. In some cases the linker (also referred to herein as a spacer) has been optimized to enhance production of the chimeric polypeptide in target host cells. In other cases, methods are provided for producing and isolating these enhanced amounts of chimeric protein in a substantially endotoxin free state.

In another aspect, the invention provides novel adjuvant compositions (which do not contain any animal derived proteins or chemicals, like benzene) and vaccines that incorporate chimeric somatostatin proteins of the invention. Embodiments include unexpectedly effective adjuvant/chimeric somatostatin protein (typically substantially endotoxin free), i.e., novel vaccines, compositions for inducing antigenicity in vaccinated target farm animals. In some embodiments the target farm animal is a dairy cow, bull calve, pig, goat, etc. Note that although the adjuvants of the present invention are described in combination with the chimeric somatostatin proteins herein, it is envisioned that the inventive adjuvants herein could be used with other vaccines and in a variety of target animals, e.g., humans, pigs, dogs, cats, etc.

In other aspects, methods are provided for vaccinating target farm animals using as few as one dose of this novel vaccine to obtain enhanced productivity, and in particular, enhanced milk production in dairy cows and other like farm animals. These improved dose procedures (fewer number of vaccinations and smaller concentration of chimeric somatostatin) provide for time effectiveness and lower costs, which when extended to the dairy industry represents a significant advancement in farm animal productivity. Also, the methods herein avoid use of recombinant growth hormone therapy which are a concern within the health care industry, i.e., both to the target farm animal, the end user and the environment where excretion of recombinant growth hormone is released into the ground water supply.

DEFINITIONS

The following definitions are provided to facilitate understanding of certain terms used frequently herein and are not meant to limit the scope of the present disclosure.

The term "amino acid" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylation, covalent attachment of flavin, ADP-ribosylation, cross-linking, iodination, methylation, and the like.

The terms "chimeric polypeptide" or fusion protein refer to a first polypeptide having attached a second, heterologous polypeptide, such that the first and second polypeptides are expressed in frame. Often the two polypeptides can be attached via a linker or spacer segment to optimize expression and function of the chimeric polypeptide(s) of the invention.

The term "endotoxin" refers to toxins associated in the cell walls of gram negative bacteria. In some cases the toxins are lipopolysaccharide components of bacterial membranes.components of outer membrane of gram negative bacteria cell walls.

The term "host cell" or "host cells" refers to cells established in ex vivo culture. It is a characteristic of host cells discussed herein that they be capable of expressing the chimeric proteins of the invention. Examples of suitable host cells useful for aspects of the invention include, but are not limited to, bacterial, yeast, insect and mammalian cells. Specific examples of such cells include SF9 insect cells (Summers and Smith, 1987, Texas Agriculture Experiment Station Bulletin, p 1555), *E. Coli* cells (BL21(DE3), Novagen), yeast (*Pichia Pastoris*, Invitrogen) and human liver cells (Hep G2 (ATCC HB8065).

The term "nucleic acid sequence" refers to the order of sequence of deoxyribonucleotides along a strand of deoxyribonucleic acid. The order of these deoxyribonucleotides determines the order of the amino acids along a polypeptide chain. The deoxyribonucleotide sequence codes for the amino acid sequence.

The terms "protein," "peptide," and "polypeptide" are used interchangeably to denote an amino acid polymer or a set of two or more interacting or bound amino acid polymers.

The term "substantially" refers to a "great extent," for example, substantially removed means that at least 75%, more typically at least 80%, 85%, 90%, 95% and most typically 96%, 97%, 98%, 99% of the target material is removed; substantially inactive means at least 75%, more typically 80%, 85%, 90%, 95% and most typically 96% 97%, 98%, 99% of an enzyme is inactivated. As such a substantially inactive CAT enzyme is one that has 75%, 80%, 85%, 90%, 95% 96%, 97%, 98%, 99% or 100% of its activity removed. (CAT activity can be determined using known functional assays, for example binding of n-Butyryl Coenzyme A to radiolabelled chloramphenicol and subsequent measurement by Liquid Scintillation Counting (LCS); by determining the amount of radioactive label transferred from [$^{14}C$acetyl CoA to chloramphenicol by thin layer chromatography (see Molecular Cloning: A Laboratory Model, $3^{rd}$ ed., J Sambrook and D W Russell, 2001. Cold Spring Harbor Press] or other known or like assays).

The term "vector" is used in reference to nucleic acid molecules that transfer DNA segment(s) from one cell to another cell. The term "vehicle" is sometimes used interchangeably with vector. Two common types of vectors are plasmids and viral vectors.

Somatostatin

A number of studies have shown that animals immunized with somatostatin have an average daily gain of 10-20%, an appetite reduced by 9% and an 11% increase in the efficiency of food utilization. Animals immunized with somatostatin, and also their offspring, have correct proportions, and the distribution of the weight of the animals between the muscles, bones and fat is the same as in control animals (see Reichlin, 1987). Therefore, somatostatin immunization provides a useful and safe way of enhancing a target animal's productivity. This is particularly the case when compared with use of recombinant growth hormone, which use has raised concerns over hormone in milk or meat from treated animals or for the safety of the animals themselves or for build-up of the hormone in the ecosystem, particularly the ground water supply.

Somatostatin-14 is a biologically active tetradecapeptide produced in the hypothalamus and gastrointestinal tract. The amino acid sequence of the tetradecapeptide is AGCKNFF-WKTFTSC (SEQ ID NO: 1). The sequence of somatostatin-14 is highly conserved among mammals (Lin X W et al. Evolution of neuroendocrine peptide systems: gonadotropin-releasing hormone and somatostatin. Comp Biochem Physiol C Pharmacol Toxicol Endocrinol. 1998 119(3):375-88.) The tetradecapeptide is encoded by a nucleic acid sequence GCTGGCTGCAAGAATTTCTTCTGGAA-GACTTTCACATCCTGT (SEQ ID NO: 2) (note that other nucleic acid sequences can be used to code SEQ ID NO: 1, however, SEQ ID NO: 2 is provided for illustrative purposes).

Somatostatin-14 is known to have a strong inhibitory effect on a large number of hormones involved in the growth and utilization of food in animals. As previously described in U.S. Pat. No. 6,316,004 (incorporated herein by reference for all uses), somatostatin-14 and chimeric versions of somatostatin can be used in immunization of animals for increase in daily weight and, where appropriate, milk production. These immunization procedures were preformed with conventional adjuvants and did not utilize the somatostatin-based materials of this invention. Note that treatment of target animals with anti-somatostatin antibodies has proven to be overly costly and functionally non-dramatic, thereby eliminating direct antibody treatment as non-practical. Muromtsev G. S., et al., 1990, Basics of agricultural biotechnology, Agropromizdat, Moscow, pp 102-106. One aspect of the present invention is based on the concept that the anti-somatostatin antibodies formed by compositions and methods described herein attenuate but do not completely eliminate the mostly inhibitory actions of somatostatin in the target animal. This process produces a natural and proportional increase in growth and productivity in immunized target animals.

As such, aspects of the present invention facilitate somatostatin based immunization by providing highly immunogenic materials for use in immunizing target animals. These somatostatin based immunization compounds have been optimized for expression and antigenicity. In some embodiments, somatostatin-14 is expressed as a codon-optimized, CAT-deficient somatostatin chimeric polypeptide. These materials provide an unexpected improvement over other immunization based vaccines.

Novel Codon-Optimized, CAT-Deficient Somatostatin Constructs

One aspect of the invention provides isolated nucleic acid molecules that encode chimeric proteins having optimized somatostatin immunogenic activity. In particular, embodiments of the invention include novel nucleic acid constructs that encode CAT fusion proteins having immunogenic activity for somatostatin. These polypeptides have been identified for optimal functional activity in immunization procedures.

In one embodiment, a construct having a schematic as shown in FIG. 1 is provided to encode the chimeric polypeptides of the invention. Nucleic acid constructs of the invention generally encode an inactive CAT enzyme without 10 C-terminal amino acids and includes one or two histidine replaced amino acids. Substantial inactivation of CAT avoids adverse reactions to CAT in the injected target animal (and thereby avoidance of CAT resistance). Note that chloramphenicol is a commonly used antibiotic in the cattle industry and resistance to chloramphenicol in cattle would be adverse to the safety of animals vaccinated using materials of the invention. As such, constructs having an inactivated CAT have the immunogenicity of CAT without the adverse side-effects of resistance in vaccinated animals (a problematic safety issue for the animals).

The CAT enzyme is inactivated by removing the imidazole group of His 193 (His 195 in the canonical $CAT_{III}$ variant, see Lewendon et al below). In another embodiment the CAT enzyme is inactivated by removing the imidazole groups of both His 193 and nearby His 192 (respectively His195 and His194 for $CAT_{III}$). Removal of the essential His193 (His195 in $CAT_{III}$) imidazole group from the active site of CAT and replacement with a alanine, glycine or other like amino acid results in substantial inactivation of the CAT enzyme (Lewendon A et al. (1994). Replacement of catalytic histidine-195 of chloramphenicol acetyl transferase: evidence for a general base role for glutamate. Biochemistry. 33(7):1944-50.). Finally, embodiments herein can also include CAT enzyme inactivation through removal of the imidazole group of His192 alone (His 194 for $CAT_{111}$). As for His193, replacement can be with an alanine, glycine or other like amino acid.

In some aspects, the one or more replaced histidine amino acids are encoded by nucleic acids located at position numbers 574-576 and 577-579 of SEQ ID NO: 3 (corresponding to amino acid numbers 192 and 193 in SEQ ID NO:4). In some embodiments the nucleic acid sequences of the invention include SEQ ID NO: 5, SEQ ID NO: 6 and SEQ ID NO:7. Chimeric proteins of the invention that include the histidine replaced constructs herein provide highly immunogenic proteins with little or no CAT activity, a significant improvement over the existing art. The substantially inactivated CAT enzyme embodiments are attached to a somatostatin polypeptide of the invention. This attachment can be made directly or with a linker (as described more fully below).

Inactivation of the target sites (His 192 and/or His 193) can be accomplished via any number of known procedures to those skilled in the art including site-directed mutagenesis and synthetic gene assembly. In one embodiment, the nucleic acid sequence that encodes histidine 193 is modified to encode an alanine, glycine or other like amino acid. In another embodiment, the nucleic acid sequences that encodes histidine 192 is modified to encode alanine, glycine or other like amino acids. Typical combination replacements for the 192 and 193 chimeric polypeptide include: alanine, alanine; alanine, glycine; glycine, alanine; and glycine, glycine.

Embodiments of the present invention also include the amino acid sequences for CAT deficient polypeptides of the invention, including amino acid sequence having SEQ ID NO: 8, 9 and 4 (corresponding to his→gly at 193, his→ala at 193, and his→gly at both 192 and 193).

As shown in FIG. 1, the substantially non-active CAT enzyme can be linked to somatostatin-14 via a variable length spacer. The spacer being required to insure presentation of the encoded somatostatin on a global surface. Spacer embodiments herein provide for optimal protease resistance and for optimal epitope exposure and inclusion in chimeric polypeptides of the invention have shown unexpected improvement over constructs not having the linker sequence(s) of the present invention.

Spacer embodiments, therefore, have been optimized in length and composition to ensure CAT-defective somatostatin expression in various microorganisms, and in particular in *E. Coli*. Original constructs as described in U.S. Pat. No. 6,316,004, included a spacer having rare *E. Coli* codons and required the co-expression of rare tRNAs from a second or helper plasmid. Spacer embodiments herein remove these rare *E. Coli* codons and thereby remove the need for a second helper plasmid, an improvement over previous technology.

In typical embodiments, the spacer has a nucleic acid sequence of tgggaactgcaccgttctggtccacgcccgcgccctcgcccacgtccggaattcatg (SEQ ID NO:10). One example of a spacer of the invention has an amino acid sequence of welhrsgprprprprpefm (SEQ ID NO:11). A typical amino acid sequence for a spacer of the invention is welhrsgp(rp)$_n$efm where n>1 (SEQ ID NO:12). As noted above, these novel spacer sequences provide for enhanced protease resistance (thereby allowing for increased production as compared to constructs disclosed in U.S. Pat. No. 6,316,004) and optimal somatostatin-14 exposure. The combination of somatostatin-14 attached to a substantially inactivated CAT enzyme (histidine replaced constructs) by an optimally configured linker showed unexpected and surprising improvement over other conventional materials when used to immunize target animals for enhanced productivity.

Although not as optimal in function, other linker sequences of variable length can be used to attach the somatostain-14 to the substantially inactive CAT enzyme. In addition, it is envisioned that a direct fusion of the somatostatin-14 to the substantially inactive CAT enzyme could also be used herein, and is considered to be within the scope of the present invention.

Vectors and Host Cells

The present invention also relates to vectors comprising the polynucleotide molecules of the invention, as well as host cells transformed with such vectors. Any of the polynucleotide molecules of the invention may be joined to a vector, which generally include a selectable marker and origin of replication, for the propagation host of interest. Host cells are genetically engineered to include these vectors and thereby express the polypeptides of the invention. Generally, vectors herein include polynucleotides molecules of the invention operably linked to suitable transcriptional or translational regulatory sequences, such as those for microbial or viral host cells. Examples of regulatory sequences include transcriptional promoters, operators, or enhancers, mRNA ribosomal binding sites, and appropriate sequences which control transcription and translation. Nucleotide sequences are operably linked when the regulatory sequences herein functionally relate to the chimeric polypeptide encoding polynucleotides of the invention.

Typical vehicles include plasmids, yeast shuttle vectors, baculovirus, inactivated adenovirus, and the like. In one embodiment the vehicle is a modified pET30b CatSom plasmid (see FIG. 1). Target host cells for use herein include bacterial host, e.g., *E. Coli.*, yeast, SF-9 insect cells, mammalian cells, plant cells, and the like.

In one embodiment, the regulatory sequences include a T7lac, CAT, Trp, or T5 promoter for expression of the chimeric polypeptides of the invention in *E. coli* or other like microbes. These regulatory sequences are known in the art and are used under appropriate and known conditions.

Where generically modified green plant cells are utilized for expression, systems as developed by Planet Biotechnology and others can be utilized.

Various plasmids of the invention have been constructed for expression of chimeric polypeptides of the invention through utilization of target regulatory sequences. Illustrative plasmids can include a T7lac promoter (see FIG. 1).

Host cells for expression of target chimeric polypeptides include prokaryotes, yeast and higher eukaryotic cells. Illustrative prokaryotic hosts include bacteria of the genera *Escherichia, Bacillus,* and *Salmonella* as well as the genera *Pseudomonas* and *Streptomyces*. In typical embodiments the host cell is of the genera *Escherichia* and can be *Escherichia Coli* (*E. Coli*).

As shown in the Examples below, constructs of the invention provide for optimal CAT deficient somatostatin expression under a variety of conditions. These constructs are particularly efficient for expression in prokaryotic hosts and in particular bacteria of the genera *Escherichia*. Note as well that various plant expression systems can also be used in the context of the present invention, typically using *Agrobacterium trameficies*.

Endotoxin Free Fusion Protein Purification

Aspects of the present invention include use of endotoxin free, codon-optimized, CAT-deficient somatostatin for use in vaccination of animals, and in particular for vaccination of farm animals, which in some cases are United States bred dairy cows. Endotoxin free materials are particularly important for cattle bred and raised in the United States (see for example, Drackley, J K 2004. Physiological adaptations in transition dairy cows. Pp 74-87 in Proc. Minnesota Dairy Herd Health Conf., St Paul, Minn. University of Minnesota, St. Paul).

In one embodiment, the chimeric immunogenic somatostatin-comprising proteins of the invention are prepared by transforming target cells with appropriate somatostatin-containing vehicles. As noted above, vehicles for use herein include known plasmid and vector systems suitable for expression in selected target cells.

In an aspect of the invention, chimeric immunogenic somatostatin-comprising proteins are expressed in target host cells. Chimeric protein expression is performed using target regulatory sequences. In some aspects the chimeric polypeptides have been optimized (especially with regard to spacer sequences disclosed herein) for expression in *E. Coli*.

Chimeric protein can then be purified in accordance with known protein purification technologies, including, for example, lysozyme lysis, differential centrifugation of inclusion bodies, sieve chromatography and the like. Refolding procedures can be conducted in guanidine chloride and urea at alkaline pH followed by dialysis and lyophilization.

In one embodiment, *E. coli* cells are transformed using the codon-optimized, CAT-deficient somatostatin containing plasmid—pET30b CatSom; the pET30b CatSom having appropriate *E. Coli* base regulatory sequences for expression. In some cases, fermentation of approximately ten liters of these cells provides at least 500 grams and in some cases 600 grams of total biomass, yielding about 4-6 grams of total protein. It is estimated from silver and coomassie blue staining that up to half of the protein can be chimeric protein (see Example 2 and FIG. 2).

In some embodiments herein, chimeric protein of the invention is purified from transformed host cells in a substantially endotoxin free state. Realization that endotoxin, and in particular multiple exposures to endotoxin, in some animals, and in particular dairy cows, results in substantially compromised animals (mastitis and endotoxin shock in dairy cows bred and raised in the United States) was an unexpected and surprising result that the present inventors obtained. This realization resulted in an attempt to remove or lower the endotoxin dose amount or number of exposures in dairy cow vaccinations. Note that this endotoxin based effect is much less realized in cows bred and raised in Russia and other countries as the dairy cattle are descendent from a different strain of cow. Holstein Association, 1 Holstein Place, Brattleboro, Vt. 05302-0808. This finding in United States dairy cows is generally contrary to the expectation that a vaccine should include some low amount of endotoxin to help maximize an animals' immune response, as is the case for dairy cows when vaccinated with somatostatin in some other European markets (see U.S. Pat. No. 6,316,004).

As such, some embodiments herein are directed at production of substantially endotoxin free chimeric proteins for use in vaccines, and especially for use in vaccines used in the cattle industry and used in the cattle industry within the United States. In certain embodiments the endotoxin levels are at or below 1 EU/ml and in other embodiments the endotoxin levels are substantially eliminated, i.e., the chimeric polypeptides of the invention are substantially endotoxin free.

In one embodiment, recovered IP from lysed host cells is washed multiple times using a wash solution devoid of endotoxin, i.e., endotoxin free water or solution. The recovered IP pellet can optionally be washed until endotoxin levels are below approximately 1 EU/ml (endotoxin tests can be performed using one or more known assays, including commercially available test kits from MP Biochemicals, Charles River, etc.). In some embodiments the wash solution is endotoxin free and includes one or more proteolytic protein inhibitor(s), e.g., phenylmethanesulphonylfluoride (PMSF), 4-(2-aminoethyl)-benzenesulphonyl fluoride (AEBSF), etc. In some embodiments the wash solution is phosphate buffered saline (PBS) having an inhibitory effective amount of PMSF, AEBSF or a combination of both PMSF and AEBSF.

In some aspects, substantially endotoxin free pellets can be treated with a protein unfolding solution at pH 12.5 containing urea and refolded in a protein refolding solution containing a reduced molarity of urea with arginine, glycerol and/or sucrose. Purified chimeric protein concentration is modified to be between 1 and 3 mg/ml and typically about 1.4 to 1.8 mg/ml. In some cases, substantially endotoxin free chimeric protein is provided to vaccine formulations at about 1.5 to 5 mg/2 ml dose and more typically from 2.0 to 3.5 mg/2 ml dose.

Other endotoxin removal procedures are envisioned to be within the scope of the present invention and can include, for example, commercially available ion-exchange endotoxin removal columns, hydrophobic columns, etc (see for example Mustang E or G Columns (Millipore)).

Enhanced Immune Response Adjuvant

Embodiments of the invention provide new adjuvants for enhanced induction of humoral immunity. These adjuvants provide a significant improvement over conventional materials for the induction of a humoral response. Adjuvants herein can be used with numerous vaccines, but are shown in the Examples in use with polypeptides of the invention for vaccination in dairy cows, pigs or bull calves.

Importantly, all components of adjuvants herein are of non-animal origin, thereby eliminating potential cross-contamination of vaccinated animals from potentially contaminated adjuvant components. For example, embodiments herein can utilize animal origin free Tween 80. This is particularly important when the target animal is a dairy cow, due to concerns over bovine spongiform encephalopathy (BSE) or other like bovine ailments. Note that these concerns are equally appropriate for human treatment where non-animal origin adjuvant provide significant safety benefits. Additionally, adjuvant embodiments herein are free of benzene and other like carcinogenic compounds. These embodiments provide a safety benefit not available in most conventional adjuvant compounds. For example, embodiments herein can utilize Carbopol® 974P or benzene free polycyclic acid.

In one embodiment, the immunological adjuvant comprises an oil-in-water emulsion in combination with selected antigens admixed within an emulsion premix.

Illustrative oil-in-water emulsions for use herein include combinations of mineral oil, Tween 80, Span 85 and target polymers (benzene-free Polyacrylic acid). In some cases the target polymer is selected from the group consisting of Carbomer Homopolymer Type B. Typical oil-water emulsions comprise from about 8-10% mineral oil (v/v), 0.003 to 0.004% Tween 80 (v/v), 0.007 to 0.008 Span 85 (v/v) and 0.04 to 0.06% polymer (w/v).

Illustrative emulsion premixes of the invention are composed of a high molecular weight polymer, surfactant, and emulsifier in at approximate 50% oil-aqueous base. High molecular weight polymers for use herein include acrylic acids crosslinked with allyl ethers of pentaerythritol. In some cases the high molecular weight polymers have a Brookfield RVT viscosity of between about 29,000 and 40,000, for example, Carbopol® 974P (Noveon, Inc).

Method for Obtaining Optimized Immune Response in Dairy Cows or Other Target Farm Animals In accordance with compositions and methods of the present invention, the immunogenic compositions described herein (endotoxin free, codon-optimized, CAT-deficient somatostatin constructs) are combined with novel adjuvants, as described above, to provide vaccines of the invention. In one embodiment, endotoxin free, codon-optimized, CAT deficient somatostatin constructs at a total dose of 2.98 mg/2 ml (of which from 5% to 25% is adjuvant (v/v), more typically from 10% to 20% is adjuvant and most typically about 20% is adjuvant) is administered. Note that other conventional adjuvants are envisioned to be within the scope of the invention and can be used with the codon-optimized, CAT-deficient somatostatin constructs of the invention, however, optimal results have been shown when the novel adjuvants herein are used in this capacity.

The purpose of the novel somatostatin constructs and adjuvant is to increase the productivity of a target animal, typically a farm animal, and more typically a dairy cow, bull calve, sheep, pig, or goat.

The preparation is injected intramuscularly or subcutaneously, preferably fewer than 12 times, more preferably fewer than 6 times, and in some cases as few as only one time. When more than one injection is required in a target animal, an interval of 14 to 28 days is typical before the next injection. As noted above, embodiments herein avoid the use of recombinant hormone treatment to target animals, a major benefit in the animal husbandry field (recombinant growth hormone has been associated with early onset of puberty in girls and various environmental concerns that the manure from treated cattle can adversely effect both surface and groundwater environments).

Sterile compositions of the invention can be administered by subcutaneous or intramuscular routes. In typical cases the site of administration is the target animal's neck or tail, although other sites may be utilized. Note that a site should be used such that an adverse reaction does not impede the animal's ability to move, eat, drink, etc.

As noted above, vaccines herein, typically in an endotoxin free state, using the novel adjuvants described herein, provide a significant improvement in meat and milk production of dairy cows, cattle, pigs, etc. These treatments, however, are not accompanied by an increase in feed consumption.

EXAMPLES

The following examples are provided for illustrative purposes only and are not intended to limit the scope of the invention.

Example 1

Construction of CAT-Defective Somatostatin Fusion Protein

The present example illustrates the production of a CAT-defective somatostatin fusion protein in accordance with embodiments of the present invention. Site-directed mutagenesis was performed on plasmid pET30b-Cat-Som to replace His192 and His193 with glycine residues (after modification: Gly192 and Gly193). Inactivation of the His193 (and His192) residues eliminates the capacity of the CAT enzyme to accept protons, thereby providing complete inactivation of the CAT.

The spacer in the same pET30b-Cat-Som (having the His replacement(s)) was codon-optimized for expression by *E. coli* in the absence of co-expressed tRNA molecules.

The modified CAT-defective somatostatin nucleic acid construct is shown as SEQ ID NO: 13. The CAT-defective somatostatin fusion protein sequence is disclosed as SEQ ID NO: 14, being compared to an unmodified CAT-somatostatin fusion protein (SEQ ID NO: 15).

Example 2

CAT-Defective Somatostatin Fusion Protein can be Expressed at High Levels

The codon-optimized CAT-defective somatostatin construct as described in Example 1 was used to express the fusion protein in BL21 (DE3) cells. Transformed cells were grown in LB and induced with 0.4 mM IPTG for approximately three hours. One milliliter of cells from a density of OD 0.7 culture were pelleted, and heated at 70° C. for ten minutes in 100 μl SDS sample buffer. A sample of 40 μl of cell extract was loaded per lane for SDS PAGE.

Figure 2:
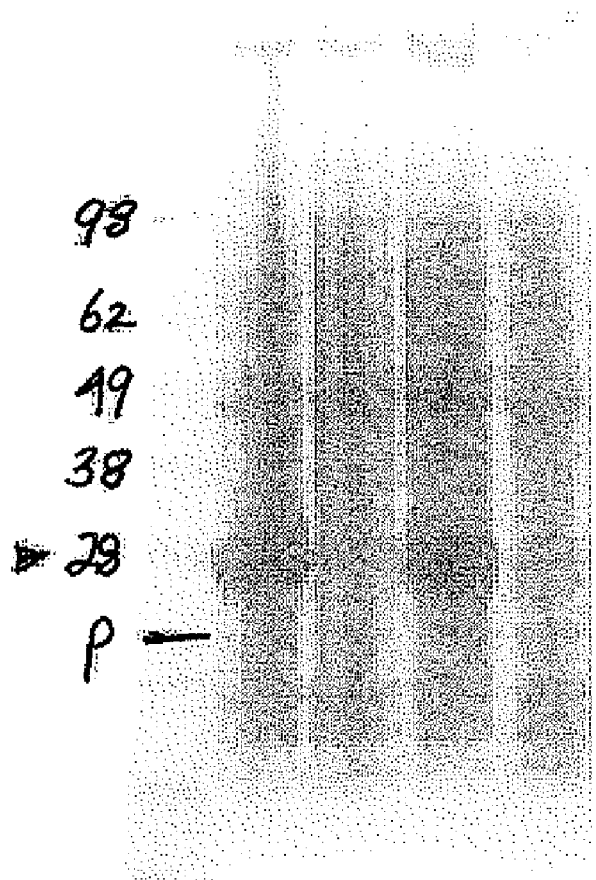
FIG. 2 is an illustrative stained SDS-PAGE showing a 28 KD band corresponding to the predicted size of a codon-optimized, CAT-defective somatostatin polypeptide of the invention. Lane 1 is LB+IPTG, reduced, Lane 2 is LB, reduced, Lane 3 is LB+IPTG and Lane 4 is LB.

As shown in FIG. 2, a 28 KD band corresponding to the predicted size of a codon-optimized, CAT-defective somatostatin fusion protein was visible in lanes 1 (LB+IPTG, reduced) and 3 (LB+IPTG) after induction with IPTG. No expression is seen in control lanes 2 (LB, reduced) and 4 (LB). As expected, there was no difference in fusion protein size when run under standard or reducing conditions.

Example 3

Endotoxin Free, Codon-Optimized CAT-Deficient Somatostatin Containing Vaccine An illustrative vaccine in accordance with the present invention:

| | | |
|---|---|---|
| a. | JH 14 (Adjuvant) | 24 ml |
| | mineral oil - 50% (v/v) | |
| | Tween 80 - 0.1694% (v/v) | |
| | Span 85 - 0.1915% (v/v) | |
| | Carbopol 974NP - 0.125% (w/v) | |
| b. | Refolded Protein of the invention | 95.6 ml |
| | (2.96 mg/ml) - see Example 2 | |
| c. | Phosphate Buffered Saline | 35.6 ml |
| d. | Antibacterial/Antifungal | 0.36 mo |
| | | 120 ml |

Example 4

Endotoxin Free Chimeric Peptides/Adjuvants Provide Increased Milk Production A random pool of dairy cows (Holstein Crosses—US bred and raised) was identified, each was 31 to 65 days post-calving ($3^{rd}$ through $5^{th}$ lactation). Each cow was examined and determined to be in optimal health by a veterinarian.

The average cow weight in the study was from about 1,000 to 1,200 lbs. Six lactating cows were treated with 1.96 mg/chimeric protein/2 ml dose in JH14. Alternatively, 9 lactating cows were provided with a conventional rBST treatment. Treatments and milk production study was conducted at a large scale, intense milk production dairy.

Vaccinations were conducted at day 0. Anti-SST serum antibodies and IGF-1 serum levels tested at 4 weeks, Milk production and identification of general health of animals were conducted on a regular schedule.

Six cows that were vaccinated using inventive compositions described herein had a normal appearance, with no endotoxin reaction or food withdrawal. All six cows had a positive serologic response to SST with a mean titer of 1:14. Milk production of the six cows was obtained with only one vaccination (see FIG. 3A), showing a mean yield increase of 23.7%.

Nine cows treated using conventional rBST injections at 0 and 14 days with an overall mean increase in milk productivity of 2% (see FIG. 3B).

The data in this Example shows the drastic improvement in effectiveness for using the endotoxin free constructs in combination with inventive adjuvants in dairy cows. These results are dramatically improved toward the animal's health and productiveness as compared to cows rejected two times with rBST.

Example 5

Endotoxin Free Chimeric Peptides/Adjuvants Provide Increased Meat Production in Piglets of Treated Sows A random pool of sows will be identified, each being at least 35-36 days prior to farrowing. Each sow will be examined and determined to be in optimal health by a veterinarian. Pregnant sows will be immunized two times using vaccines of the invention (see Example 3), once at 35-36 days prior to delivery, and once at 8 days prior to delivery. A control group of pregnant sows will be maintained for comparison purposes (no vaccinations or vaccination with sterile saline).

Delivered piglets from the vaccinated group will have greater survivability and be of a greater average size. It is the increase in piglet size that enhances the percent survivability, as larger piglets are less likely to be pushed away from the sow's teat. Treated and control piglets will be weighed at day 21, day 30 and day 75. Vaccinations of the present invention will increase the piglet daily weight by an average of 35% over the course of the 75 day period.

Importantly, piglet survivability and weight are increased through use of the vaccines of the present invention in the absence of recombinant growth hormone. This is a significant improvement over recombinant hormone therapy.

Example 6

Endotoxin Free Chimeric Peptide/Adjuvants Provide Increased Meat Production in Treated Bull Calves A random pool of bull calves, one to three months of age, will be identified, and injected with compositions of the invention. Weight increase over a period of approximately ten months will be monitored and compared to a control group, the control group being treated the same in every sense as the injected group except for the vaccine injections of the invention. Each bull calve will be examined and determined to be in optimal health by a veterinarian over the course of the treatments.

Injections herein for the vaccinated group are performed at zero weeks, 4 weeks and 8 (three total vaccinations). Vaccinations will be provided subcutaneously or intramuscularly to the neck using 18-21 gauge cc needle. Booster injections were also provided (4 boosts, three boosts or no boosts). Vaccination injections included 2 mg/2 ml of the chimeric polypeptide. The chimeric polypeptide was prepared as described herein having both histidine residues in CAT replaced with glycine amino acids of the invention and a optimized linker as described by SEQ ID NO: 4.

Vaccinated bull calves and control calves are each weighed to take an initial weight. It is expected that vaccinated animals herein will show a 15 to 40% weight increase over control animals. This increase in average weight for treated bull calves shows a significant advantage over no treatment.

Importantly, harvested meat from treated bull calves does not contain recombinant growth hormone.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A composition comprising:
   a chimeric polypeptide comprising a somatostatin-14 polypeptide represented by SEQ ID NO: 1 and a chloramphenicol acetyl transferase polypeptide having a sequence selected from the group consisting of SEQ ID NO: 4, SEQ ID NO: 8, and SEQ ID NO: 9,
   wherein the composition is substantially endotoxin free.

2. The composition of claim 1, wherein the composition is at least 80% endotoxin free.

3. The composition of claim 1, wherein the chimeric polypeptide has an amino acid sequence with at least 90% sequence identity to SEQ ID NO: 14.

4. The composition of claim 1, wherein the chimeric polypeptide has an amino acid sequence of SEQ ID NO: 14.

5. The composition of claim 1, formulated for use as a vaccine.

6. The composition of claim 1, wherein the chloramphenicol acetyl transferase polypeptide lacks enzymatic activity.

7. The composition of claim 1, wherein the somatostatin-14 polypeptide and the inactive chloramphenicol acetyl transferase polypeptide are linked by a spacer.

8. The composition of claim 7, wherein the spacer comprises a sequence selected from the group consisting of SEQ ID NO: 11 or SEQ ID NO: 12.

9. The composition of claim 1, further comprising an adjuvant.

10. The composition of claim 9, further comprising one or more antigens selected from the group consisting of native polypeptides, recombinant polypeptides, synthetic polypeptides, polysaccharides, and glycoproteins.

11. A composition comprising:
   a chimeric polypeptide comprising a somatostatin-14 polypeptide represented by SEQ ID NO: 1 and a chloramphenicol acetyl transferase polypeptide,
   wherein the chloramphenicol acetyl transferase polypeptide is modified at the 192 residue, at the 193 residue, or at both 192 and 193 residues, relative to the wild type chloramphenicol acetyl transferase polypeptide represented by residues 1-210 of SEQ ID NO: 15, and
   wherein the modification comprises replacement of one or both histidines independently with glycine or alanine.

12. The composition of claim 11, wherein the modification comprises replacement of histidine at the 193 residue to a glycine.

13. The composition of claim 11, wherein the modification comprises replacement of histidine at the 193 residue to an alanine.

14. The composition of claim 11, wherein the modification comprises replacement of histidine at the 192 residue to a glycine and histidine at the 193 residue to a glycine.

15. The composition of claim 11, wherein the chloramphenicol acetyl transferase polypeptide is truncated at the C-terminus by 10 amino acids relative to the wild type polypeptide.

16. The composition of claim 11, wherein the composition is substantially endotoxin free.

17. The composition of claim 11, wherein the composition is at least 80% endotoxin free.

* * * * *

```
                         SEQUENCE LISTING

<160> NUMBER OF SEQ ID NOS: 15

<210> SEQ ID NO 1
<211> LENGTH: 14
<212> TYPE: PRT
<213> ORGANISM: Artificial
<220> FEATURE:
<223> OTHER INFORMATION: Synthetic

<400> SEQUENCE: 1

Ala Gly Cys Lys Asn Phe Phe Trp Lys Thr Phe Thr Ser Cys
1               5                   10

<210> SEQ ID NO 2
<211> LENGTH: 42
<212> TYPE: DNA
<213> ORGANISM: Artificial
<220> FEATURE:
<223> OTHER INFORMATION: Synthetic

<400> SEQUENCE: 2
gctggctgca agaatttctt ctggaagact ttcacatcct gt                          42

<210> SEQ ID NO 3
<211> LENGTH: 630
<212> TYPE: DNA
<213> ORGANISM: Artificial
<220> FEATURE:
<223> OTHER INFORMATION: Synthetic

<400> SEQUENCE: 3
atggagaaaa aaatcactgg atataccacc gttgatatat cccaatggca tcgtaaagaa        60
cattttgagg catttcagtc agttgctcaa tgtacctata accagaccgt tcagctggat       120
attacggcct tttaaagac cgtaaagaaa ataagcaca agtttatcc ggcctttatt          180 cacattcttg cccgcctgat gaatgctcat ccggaattcc gtatggcaat gaaagacggt       240
gagctggtga tatgggatag tgttcaccct tgttacaccg ttttccatga gcaaactgaa       300
acgttttcat cgctctggag tgaataccac gacgatttcc ggcagtttct acacatatat       360
tcgcaagatg tggcgtgtta cggtgaaaac ctggcctatt tccctaaagg gtttattgag       420
aatatgtttt tcgtctcagc caatccctgg gtgagtttca ccagttttga tttaaacgtg       480
gccaatatgg acaacttctt cgccccgtt ttcaccatgg gcaaatatta tacgcaaggc       540
gacaaggtgc tgatgccgct ggcgattcag gttggtggtg ccgtttgtga tggcttccat       600
```

```
gtcggccgta tgcttaatga actgcagcag                                       630
```

<210> SEQ ID NO 4
<211> LENGTH: 210
<212> TYPE: PRT
<213> ORGANISM: Artificial
<220> FEATURE:
<223> OTHER INFORMATION: Synthetic

<400> SEQUENCE: 4

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val Gly
            180                 185                 190

Gly Ala Val Cys Asp Gly Phe His Val Gly Arg Met Leu Asn Glu Leu
        195                 200                 205

Gln Gln
    210
```

<210> SEQ ID NO 5
<211> LENGTH: 630
<212> TYPE: DNA
<213> ORGANISM: Artificial
<220> FEATURE:
<223> OTHER INFORMATION: Synthetic

<400> SEQUENCE: 5

```
atggagaaaa aaatcactgg atataccacc gttgatatat cccaatggca tcgtaaagaa     60
cattttgagg catttcagtc agttgctcaa tgtacctata accagaccgt tcagctggat    120
attacggcct ttttaaagac cgtaaagaaa aataagcaca gtttatatcc ggcctttatt    180
cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
```
gccaatatgg acaacttctt cgcccccgtt ttcaccatgg gcaaatatta tacgcaaggc    540
gacaaggtgc tgatgccgct ggcgattcag gttcatggtg ccgtttgtga tggcttccat    600
gtcggccgta tgcttaatga actgcagcag                                     630

```
<210> SEQ ID NO 6
<211> LENGTH: 630
<212> TYPE: DNA
<213> ORGANISM: Artificial
<220> FEATURE:
<223> OTHER INFORMATION: Synthetic

<400> SEQUENCE: 6
```
atggagaaaa aaatcactgg atataccacc gttgatatat cccaatggca tcgtaaagaa     60
cattttgagg catttcagtc agttgctcaa tgtacctata accagaccgt tcagctggat    120
attacggcct ttttaaagac cgtaaagaaa aataagcaca gtttttatcc ggcctttatt    180
cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt ccctaaagg gtttattgag     420 aatatgtttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttcatgctg ccgtttgtga tggcttccat    600
gtcggccgta tgcttaatga actgcagcag                                     630

```
<210> SEQ ID NO 7
<211> LENGTH: 630
<212> TYPE: DNA
<213> ORGANISM: Artificial
<220> FEATURE:
<223> OTHER INFORMATION: Synthetic

<400> SEQUENCE: 7
```
atggagaaaa aaatcactgg atataccacc gttgatatat cccaatggca tcgtaaagaa     60
cattttgagg catttcagtc agttgctcaa tgtacctata accagaccgt tcagctggat    120
attacggcct ttttaaagac cgtaaagaaa aataagcaca gtttttatcc ggcctttatt    180
cacattcttg cccgcctgat gaatgctcat ccggaattcc gtatggcaat gaaagacggt    240
gagctggtga tatgggatag tgttcaccct tgttacaccg ttttccatga gcaaactgaa    300
acgttttcat cgctctggag tgaataccac gacgatttcc ggcagtttct acacatatat    360
tcgcaagatg tggcgtgtta cggtgaaaac ctggcctatt ccctaaagg gtttattgag     420 aatatgtttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttcatggtg ccgtttgtga tggcttccat    600
gtcggcagaa tgcttaatga actgcagcag                                     630

```
<210> SEQ ID NO 8
<211> LENGTH: 210
<212> TYPE: PRT
<213> ORGANISM: Artificial
<220> FEATURE:
<223> OTHER INFORMATION: Synthetic

<400> SEQUENCE: 8
```

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
        130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

Gly Ala Val Cys Asp Gly Phe His Val Gly Arg Met Leu Asn Glu Leu
        195                 200                 205

Gln Gln
    210

<210> SEQ ID NO 9
<211> LENGTH: 210
<212> TYPE: PRT
<213> ORGANISM: Artificial
<220> FEATURE:
<223> OTHER INFORMATION: Synthetic

<400> SEQUENCE: 9

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
        130                 135                 140

Val Ser Ala Asn Pro Trp Val Ser Phe Thr Ser Phe Asp Leu Asn Val
```

```
                    145                 150                 155                 160
Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

Ala Ala Val Cys Asp Gly Phe His Val Gly Arg Met Leu Asn Glu Leu
        195                 200                 205

Gln Gln
    210

<210> SEQ ID NO 10
<211> LENGTH: 57
<212> TYPE: DNA
<213> ORGANISM: Artificial
<220> FEATURE:
<223> OTHER INFORMATION: Synthetic

<400> SEQUENCE: 10
tgggaactgc accgttctgg tccacgcccg cgccctcgcc cacgtccgga attcatg        57

<210> SEQ ID NO 11
<211> LENGTH: 19
<212> TYPE: PRT
<213> ORGANISM: Artificial
<220> FEATURE:
<223> OTHER INFORMATION: Synthetic

<400> SEQUENCE: 11

Trp Glu Leu His Arg Ser Gly Pro Arg Pro Arg Pro Arg Pro Arg Pro
1               5                   10                  15

Glu Phe Met

<210> SEQ ID NO 12
<211> LENGTH: 13
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(10)
<223> OTHER INFORMATION: The pair of residues repeats at least once

<400> SEQUENCE: 12

Trp Glu Leu His Arg Ser Gly Pro Arg Pro Glu Phe Met
1               5                   10

<210> SEQ ID NO 13
<211> LENGTH: 729
<212> TYPE: DNA
<213> ORGANISM: Artificial
<220> FEATURE:
<223> OTHER INFORMATION: Synthetic

<400> SEQUENCE: 13
atggagaaaa aaatcactgg atataccacc gttgatatat cccaatggca tcgtaaagaa        60
cattttgagg catttcagtc agttgctcaa tgtacctata accagaccgt tcagctggat       120
attacggcct ttttaaagac cgtaaagaaa aataagcaca gtttatccg gcctttatt        180 cacattcttg cccgcctgat gaatgctcat ccggaattcc gtatggcaat gaaagacggt       240
gagctggtga tatgggatag tgttcaccct tgttacaccg ttttccatga gcaaactgaa       300
acgttttcat cgctctggag tgaataccac gacgatttcc ggcagttttct acacatatat      360
```

```
tcgcaagatg tggcgtgtta cggtgaaaac ctggcctatt tccctaaagg gtttattgag    420
aatatgtttt tcgtctcagc caatccctgg gtgagtttca ccagtttga tttaaacgtg     480 gccaatatgg acaacttctt cgcccccgtt ttcaccatgg gcaaatatta tacgcaaggc    540
gacaaggtgc tgatgccgct ggcgattcag gttggtggtg ccgtttgtga tggcttccat    600
gtcggccgta tgcttaatga actgcagcag tgggaactgc accgttctgg tccacgcccg    660
cgccctcgcc cacgtccgga attcatggcc ggctgcaaga acttcttttg gaaaaccttt    720
acgagctgc                                                            729
```

<210> SEQ ID NO 14
<211> LENGTH: 243
<212> TYPE: PRT
<213> ORGANISM: Artificial
<220> FEATURE:
<223> OTHER INFORMATION: Synthetic

<400> SEQUENCE: 14

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val Gly
            180                 185                 190

Gly Ala Val Cys Asp Gly Phe His Val Gly Arg Met Leu Asn Glu Leu
        195                 200                 205

Gln Gln Trp Glu Leu His Arg Ser Gly Pro Arg Pro Arg Pro
    210                 215                 220

Arg Pro Glu Phe Met Ala Gly Cys Lys Asn Phe Phe Trp Lys Thr Phe
225                 230                 235                 240

Thr Ser Cys
```

<210> SEQ ID NO 15
<211> LENGTH: 243
<212> TYPE: PRT
<213> ORGANISM: Artificial
<220> FEATURE:
<223> OTHER INFORMATION: Synthetic

<400> SEQUENCE: 15

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20              25                  30

Tyr Asn Gln Thr Val Gln Leu Asp Ile Thr Ala Phe Leu Lys Thr Val
            35              40              45

Lys Lys Asn Lys His Lys Phe Tyr Pro Ala Phe Ile His Ile Leu Ala
        50              55              60

Arg Leu Met Asn Ala His Pro Glu Phe Arg Met Ala Met Lys Asp Gly
65              70              75                          80

Glu Leu Val Ile Trp Asp Ser Val His Pro Cys Tyr Thr Val Phe His
                85              90                      95

Glu Gln Thr Glu Thr Phe Ser Ser Leu Trp Ser Glu Tyr His Asp Asp
            100             105             110

Phe Arg Gln Phe Leu His Ile Tyr Ser Gln Asp Val Ala Cys Tyr Gly
        115             120             125

Glu Asn Leu Ala Tyr Phe Pro Lys Gly Phe Ile Glu Asn Met Phe Phe
        130             135             140

Val Ser Ala Asn Pro Trp Val Ser Phe Thr Ser Phe Asp Leu Asn Val
145             150             155                         160

Ala Asn Met Asp Asn Phe Phe Ala Pro Val Phe Thr Met Gly Lys Tyr
                165             170             175

Tyr Thr Gln Gly Asp Lys Val Leu Met Pro Leu Ala Ile Gln Val His
            180             185             190

His Ala Val Cys Asp Gly Phe His Val Gly Arg Met Leu Asn Glu Leu
        195             200             205

Gln Gln Trp Glu Leu His Arg Ser Gly Pro Arg Pro Arg Pro Arg Pro
        210             215             220

Arg Pro Glu Phe Met Ala Gly Cys Lys Asn Phe Phe Trp Lys Thr Phe
225             230             235             240

Thr Ser Cys
```